United States Patent [19]

Ahmed et al.

[11] Patent Number: 5,690,910
[45] Date of Patent: Nov. 25, 1997

[54] METHOD FOR TREATING ASTHMA

[75] Inventors: Tahir Ahmed, Coral Gables; Samuel Broder; John K. Whisnant, both of Ft. Lauderdale, all of Fla.

[73] Assignee: Baker Norton Pharmaceuticals, Inc., Miami, Fla.

[21] Appl. No.: 516,786

[22] Filed: Aug. 18, 1995

[51] Int. Cl.[6] ................................................. A61K 9/12
[52] U.S. Cl. ........................ 424/45; 424/46; 514/56; 514/826
[58] Field of Search ..................... 424/45, 46; 514/826, 514/56

[56] References Cited

PUBLICATIONS

Ahmed, et al., *American Physiol. Soc.*, pp. 893–901 (1994).
Ahmed, *Resp. Drug Delivery IV*, pp. 55–63 (1994).
Ahmed, et al., *American Physiol. Soc.*, pp. 1492–1498 (1993).
Ahmed, et al., *N. Engl. J. Med.*, vol. 329, pp. 90–95 (1993).
Ahmed, et. al., *Am. Rev. Respir. Dis.*, vol. 145, pp. 566–570 (1992).
Karnovsky et al., *Airwaves and Vascular Remodelling*, pp. 45–69 (1994).
Ashkin, et al., *Am. Rev. Resp. Dis.*, vol. 147, No. 4, p. A660 (1993).
Lucio, et al., *American Physiol. Soc.*, pp. 1093–1101 (1992).
Page, *Lancet*, vol. 337, pp. 717–720 (1991).

*Primary Examiner*—Raj Bawa
*Attorney, Agent, or Firm*—Kirschstein, Ottinger, Israel & Schiffmiller, P.C.

[57] ABSTRACT

A method of treating a patient suffering from antigen-induced asthma who has been challenged with an antigen, or providing chronic treatment to an asthma patient to reduce airway hyperresponsiveness, comprising intrabronchial administration to the patient of a pharmaceutical composition containing in each dose about 0.05 to about 1.0 mg of ultra-low molecular weight heparins (ULMWH), having an average molecular weight of 3,000 daltons or less, per kilogram of patient body weight. Inhalant pharmaceutical compositions for use in the novel treatment method are also provided.

20 Claims, 11 Drawing Sheets

METHOD FOR TREATING ASTHMA

REFERENCE TO DISCLOSURE DOCUMENT

This application incorporates material included in Disclosure Document No. 377066, filed in the Patent and Trademark Office on Jun. 23, 1995.

BACKGROUND OF THE INVENTION

1. Field of the Invention

The invention relates to methods and compositions for preventing and reversing the symptoms and manifestations of asthma.

2. Description of the Prior Art

Chronic asthma can be considered to be predominantly an inflammatory disease with associated bronchospasm. The degree of reactivity and narrowing of the bronchi in response to stimuli is greater in asthmatics than in normal individuals. Persistent inflammation is responsible for the bronchial hyperreactivity or airway hyperresponsiveness. Mucosal edema and mucus plugging and hypersecretion may be present; pulmonary parenchyma is normal. Airway narrowing may reverse spontaneously or with therapy. Type 1 (immediate) immune responses may play an important role in the development of asthma in children and many adults; however, when onset of disease occurs in adulthood, allergic factors may be difficult to identify. Exposure to cold dry air, exercise and other aggravating factors also may trigger asthma.

The most common symptoms of asthma are breathlessness and chest tightness; wheezing, dyspnea, and cough also are prominent. Reduced pulmonary function typical of obstructive rather than restrictive airway disease is usually observed. Asymptomatic periods often alternate with paroxysms.

Of the known triggers of asthma, allergens and exercise have received the most attention. Both are powerful, naturally occurring stimuli; exercise is a potential factor in the daily life of every asthmatic, whereas allergens only affect some persons with asthma. Nevertheless, more is known about the effects of antigen.

The general goals of drug therapy for asthma are prevention of bronchospasm and long-term control of bronchial hyperreactivity. Because it is usually not possible for either patient or physician to predict when bronchospasm may occur, patients with all but the most episodic and/or entirely seasonal attacks may require continuous therapy.

Beta agonists are useful as bronchodilator agents; they stimulate $beta_2$-adrenergic receptors, increase intracellular cAMP, and may inhibit the release of mast cell mediators. Other useful drugs include theophylline and related xanthine drugs, which produce bronchodilation through unknown mechanisms; the biscromone, cromolyn, which prevents the release of mediator substances and blocks respiratory neuronal reflexes, and corticosteroids, which primarily decrease inflammation and edema. Anticholinergic drugs may relieve bronchospasm by blocking parasympathetic cholinergic impulses at the receptor level. Antihistamines occasionally prevent or abort allergic asthmatic episodes, particularly in children, but they can only be partially effective in asthma because histamine is only one of many mediators.

The current drug modalities used for treatment of allergy-induced asthma suffer from a number of drawbacks. In general, the conventional agents have a relatively short duration of action and may be partially or wholly ineffective when administered after antigen challenge occurs.

Moreover, because of serious adverse effects associated with the use of agents such as $beta_2$-adrenergic agonists and corticosteroids, the therapeutic margin of safety with such agents is relatively narrow and patients using them must be carefully monitored.

Bronchial hyperreactivity (or airway hyperresponsiveness) is a hallmark of asthma and is closely related to underlying airway inflammation. Worsening of asthma and airway inflammation is associated with increase in bronchial hyperreactivity, which can be induced by both antigenic and non-antigenic stimuli. $Beta_2$-adrenergic agonists are potent agents for the treatment of bronchospasm, but have no effect on airway inflammation or bronchial hyperreactivity. In fact, chronic use of $beta_2$-adrenergic agents alone, by causing down regulation of $beta_2$-receptors, may worsen bronchial hyperreactivity. At present, corticosteroids are the only effective agents available which diminish bronchial hyperreactivity. Although inhaled corticosteroids are relatively safe in adult patients with asthma, these agents have tremendous toxicity in children, including adrenal suppression and reduced bone density and growth. Thus, the search for safer and effective agents which diminish bronchial hyperreactivity continues.

It has been discovered in the past several years that heparin administered intrabronchially can be an effective inhibitor of bronchospasm and bronchoconstriction and is consequently of value in the prophylaxis of asthma (see, e.g., Ahmed et al., *New Eng. J. Med.*, 329:90–95, 1993; Ahmed, *Resp. Drug Deliv.*, IV:55–63, 1994). It has been discovered further that low molecular weight heparins, e.g., heparins with an average molecular weight of 4,000–5,000 daltons, effectively prevent antigen-induced bronchoconstriction; these low-weight heparins also exhibit considerably less anticoagulant activity than commercial heparin, a desirable property when these agents are used in the treatment of asthma (see Ashkin et al., *Am. Rev. Resp. Dis.*, 1993 Intl. Conf. Abstracts, p. A660).

While various heparins have been found useful as prophylactic agents when administered prior to antigen challenge, however, they have been disclosed in the prior art as ineffective when administered after antigen challenge in modifying bronchoconstrictor response and airway hyperresponsiveness (Ahmed et al., *J. Appl. Physiol.*, 76:893–901, 1994).

SUMMARY OF THE INVENTION

It is an object of the present invention to provide a method and compositions for treatment of antigen-induced asthma and bronchial hyperreactivity which do not suffer from the drawbacks of the prior art.

It is a further object of the present invention to provide a method and compositions for the treatment of asthma which are effective in preventing and reversing the manifestations of an asthmatic episode.

Still another object of the present invention is to provide a method and compositions as described above which are highly effective in diminishing specific and non-specific bronchial hyperreactivity, and even when administered after antigen challenge to the patient.

In keeping with these objects and others which will become apparent hereinafter, the invention resides in a method of treating a patient suffering from antigen-induced asthma through the intrabronchial administration to the patient of a pharmaceutical composition comprising from about 0.05 to about 1.0 mg of ultra-low molecular weight heparins per kilogram of patient body weight in each dose.

The administration of these heparins can be on an acute basis following antigen challenge or on a chronic basis to suppress bronchial hyperreactivity.

The ultra-low molecular weight heparins used in the present invention have average molecular weights of less than 3,000 daltons and may exhibit a low level of anticoagulant activity or substantially no anticoagulant activity at all. Novel inhalant compositions are also provided in the form of liquid or powdered nebulizer or aerosol compositions containing suitable concentrations of ultra-low molecular weight heparins.

BRIEF DESCRIPTION OF THE DRAWINGS

$SR_L$=Specific lung resistance

+=Significantly different from antigen control (P<0.05)

$PD_4$=Cumulative provocating dose of carbachol, increasing $SR_L$ to 400% above baseline +=Significantly different from antigen alone (P<0.05).

+=Significantly different from Fragmin (P<0.05)

*=Significantly different from CY216 (P<0.05).

+=Significantly different from baseline (P<0.05)

DETAILED DESCRIPTION OF THE INVENTION

Heparin, a sulfated mucopolysaccharide, is synthesized in mast cells as a proteoglycan and is particularly abundant in the lungs of various animals. Heparin is not a specific compound of fixed molecular weight but is actually a heterogenous mixture of variably sulfated polysaccharide chains composed of repeating units of D-glucosamine and either L-iduronic or D-glucuronic acids. The average molecular weight of heparin isolated from animal tissues ranges from about 6,000 to about 30,000 daltons.

Pharmacologically, heparin is known primarily as an anticoagulant. This activity results from heparin's ability to bind to some of the residues of antithrombin III (AT-III), accelerating the neutralization by AT-III of activated clotting factors and preventing the conversion of prothrombin to thrombin. Larger amounts of heparin can inactivate thrombin and earlier clotting factors, preventing conversion of fibrinogen to fibrin.

The anticoagulant activity of heparin is related to the molecular weight of its polysaccharide fragments; low molecular weight components or fragments (for example, fragments having a molecular weight of less than 6,000 daltons) have moderate to low antithrombin and hemorrhagic effects. Similarly, low molecular weight heparins isolated from animal tissue have reduced anticoagulant properties because they consist primarily of the lower molecular weight fragments or fractions.

Commercial heparin, which is generally derived from beef lung or pork intestinal mucosa, has an average molecular weight of about 15,000–17,500 daltons.

Heparin has been shown to act as a specific blocker of the $IP_3$ receptors and inhibits $IP_3$ mediated calcium release. We have previously suggested that heparin may block $IP_3$ receptors in mast cells and therefore by interfering with signal transduction may modulate mast cell degranulation and mediator release. In vivo and in vitro studies support this concept and have demonstrated that inhaled heparin can attenuate allergic bronchoconstriction in sheep, prevent exercise induced asthma, as well as inhibit anti IgE induced mast cell histamine release. Inhaled heparin in doses up to 1,000 units/kg has been found to have no effect on partial thromboplastin time (PTT), thus, suggesting a "non-anticoagulant" effect.

It has also been reported that low molecular weight heparins (average molecular weight about 4,500 daltons), which have reduced APTT activity, were effective in animal studies in preventing antigen-induced acute bronchoconstrictor response (ABR) and bronchial hyperreactivity, also referred to as airway-hyperresponsiveness (AHR). However, as discussed and illustrated in greater detail below, neither commercial heparin nor medium or low molecular weight heparins, even those with very low anticoagulant activity, are effective in ameliorating AHR subsequent to antigen challenge in test subjects. These heparins apparently provide only a prophylactic, preventive effect, but are not of value in treating an antigen-triggered asthmatic episode.

It has now been discovered, surprisingly, that ultra-low molecular weight heparin (ULMWH) fractions are not only effective inhibitors of airway anaphylaxis, but are highly effective in reducing AHR even when administered after antigen challenge. Chronic, regular use of ULMWH should also reduce AHR, and ULMWH therefore may be used for chronic therapy of asthma whether caused by specific (i.e., antigenic) or non-specific factors.

Accordingly, the present invention constitutes a method of treating a patient suffering from antigen-induced asthma who has been challenged with an asthma-inducing antigen comprising the intrabronchial administration to the patient of a pharmaceutical composition containing about 0.05 to about 1.0 mg of one or more ULMWH fractions per kilogram of patient body weight in each dose of said composition, and preferably from about 0.075 to about 0.75 mg/kg per dose. For purposes of this application, ULMWH may be defined as heparin fractions having an average molecular weight of 3,000 daltons or less. ULMWH having an average molecular weight of 2,500 daltons or less may be even more effective when used in the method of the invention. Each ULMWH fraction may comprise disaccharides, trisaccharides, tetrasaccharides and/or pentasaccharides, as well as molecules of greater chain length.

In accordance with the invention, a patient suffering from antigen-induced asthma who has inhaled, ingested or otherwise come into contact with an antigen (i.e., has been "challenged" with an antigen) of a type known to provoke asthmatic episodes in that patient, whether or not the patient is already exhibiting symptoms of ABR and/or AHR, is promptly administered via inhalation one dose of a pharmaceutical composition containing one or more ULMWH fractions cumulatively present in the above-described concentration ranges. Additional doses may subsequently be administered as necessary until the patient regains or maintains normal airflow resistance levels.

The invention also comprehends the chronic administration of ULMWH to asthma patients to reduce and suppress AHR. "Chronic administration" as used herein refers to administration of the ULMWH-containing compositions at least once daily for at least ten consecutive days. Chronic administration of a composition containing from about 0.05–1.0 mg/kg per dose, and preferably about 0.075–0.75 mg/kg per dose, can be continued indefinitely to provide AHR-suppressant therapy at least comparable to corticosteroids but substantially without side effects.

Despite the known activity of N-desulfated heparins in other biological systems, for example as inhibitors of cell growth, it has been found that ULMWH fractions which are active and can be used in the present invention for treating asthmatic patients are all N-sulfated; N-desulfated fractions are ineffective.

The inhalant ULMWH compositions used in the present invention may comprise liquid or powdered compositions containing ULMWH and suitable for nebulization and intrabronchial use, or aerosol compositions administered via an aerosol unit dispensing metered doses.

Suitable liquid compositions comprise ULMWH in an aqueous, pharmaceutically acceptable inhalant solvent, e.g., isotonic saline or bacteriostatic water. The solutions are administered by means of a pump or squeeze-actuated nebulized spray dispenser, or by any other conventional means for causing or enabling the requisite dosage amount of the liquid composition to be inhaled into the patient's lungs.

Suitable powder compositions include, by way of illustration, powdered preparations of heparin thoroughly intermixed with lactose or other inert powders acceptable for intrabronchial administration. The powder compositions can be administered via an aerosol dispenser or encased in a breakable capsule which may be inserted by the patient into a device that punctures the capsule and blows the powder out in a steady stream suitable for inhalation.

Aerosol formulations for use in the subject method would typically include fluorinated alkane propellants, surfactants and co-solvents and may be filled into aluminum or other conventional aerosol containers which are then closed by a suitable metering valve and pressurized with propellant.

The total concentration of ULMWH fractions in any vehicle suitable for use in accordance with the present invention must be sufficiently high to provide the required dose of about 0.05 to 1.0 mg of ULMWH/kg. Thus, for example, if a nebulizer administers 4 ml of solution per dose, the concentration of ULMWH in the solution in the case of a patient weighing 75 kg should be approximately 1.0–20.0 mg/ml.

As those skilled in the pharmaceutical arts will appreciate, many conventional methods and apparatus are available for administering precisely metered doses of intrabronchial medicaments and for regulating the desired dosage amount in accordance with patient weight and severity of the patient's condition. Moreover, there are many art-recognized liquid, powdered and aerosol vehicles suitable for the intrabronchial ULMWH compositions of the present invention. The invention is not limited to any particular inert vehicles, solvents, carriers or excipients and is not restricted to any particular methods or apparatus for intrabronchial administration.

The ULMWH compositions described herein provide highly effective treatment for antigen-induced asthma even after antigen challenge has occurred.

To demonstrate the unexpected superiority of ULMWH fractions in comparison with higher molecular weight heparins in treating antigen induced asthma after antigen challenge, experiments were conducted comparing the effects of different heparin types on allergic sheep, both before and after antigen challenge. Detailed descriptions of these experiments and of the results obtained are set forth in the following examples as well as in the figures shown in the drawings.

The following examples, while illustrating the method of the invention and demonstrating the efficacy of the same, are not intended to set forth specific materials, procedures or dosage regimens which must be utilized exclusively in order to practice the invention.

EXAMPLE I

Administration of Heparins Prior to Antigen Challenge

Methods

Pulmonary Airflow Resistance:

Sixteen allergic sheep, with previously documented only acute bronchoconstrictor response to *Ascaris suum* antigen were used for all studies. The sheep were intubated with a cuffed nasotracheal tube and pulmonary airflow resistance ($R_1$) was measured by the esophageal balloon catheter technique, while thoracic gas volume was measured by body plethysmography. Data was expressed as specific $R_L$ ($SR_L$, defined as $R_L$ times thoracic gas volume ($V_{tg}$).

Airway Responsiveness:

To assess airway responsiveness, cumulative dose-response curves to inhaled cabachol were performed by measuring $SR_L$ before and after inhalation of buffered saline and after each administration of 10 breaths of increasing concentrations of carbachol (0.25, 0.5, 1.0, 2.0 and 4.0% wt/vol solution). Airway responsiveness was measured by determining the cumulative provocation dose ($PD_4$) of carbachol (in breath units) that increased $SR_L$ to 400% above baseline. One breath unit was defined as one breath of 1% carbachol solution.

Heparin Fractions:

In the experiment comparing the effectiveness of various heparin materials administered to the allergic sheep prior to antigen challenge one ULMWH (CY222, Sanofi, Paris, France), one low molecular weight heparin (CY216, Sanofi) and one medium molecular weight heparin (Fragmin, Kabivitrum, Stockholm, Sweden) were used. The molecular weight and other characteristics of these heparin fractions are set forth in Table 1.

TABLE 1

MOLECULAR WEIGHT AND CHARCTERISTICS OF HEPARIN FRACTIONS

|  | CY222 (ULMWH) | CY216 (LMWH) | FRAGMIN (MMWH) |
|---|---|---|---|
| Molecular Wt. | 2355 d | 4270 d | 6400 d |
| Anti-Xa activity | 70 I.U./mg | 112 I.U./mg | 158 I.U./mg |
| Anti-IIa activity | 12 I.U./mg | 29 I.U./mg | — |
| APTT | 28 I.U./mg | 45 I.U./mg | 58 I.U./mg |
| Anti-Xa/APTT ratio | 2.5 | 2.5 | 2.72 |
| % GAG Content | 70% | 60% | 65% |
| % of ULMW chains (m.w. < 2500 d) | 88% | 27% | 11% |

As indicated in the table, the ULMWH utilized in this experiment not only has a molecular weight well below 3,000, but in addition about 88% of the heparin chains included in this fraction have molecular weights below 2,500.

Experimental Protocol

Airway Studies

Each animal's baseline airway responsiveness ($PD_4$) was determined, and then on different experimental days the sheep underwent airway challenge with Ascaris suum antigen. $SR_L$ was measured, before and immediately after challenge, and then hourly for up to 2 hours until $SR_L$ had returned to the baseline. The post-challenge $PD_4$ was then measured. The protocol was repeated at least 14 days later, after pretreatment with aerosolized CY222, CY216, and Fragmin, at doses of 0.31, 0.62, 1.25, 2.5, and 5.0 mg/kg.

Data Analysis:

Data were expressed as (a) mean±SE % change of $SR_L$; (b) $PD_4$ as % of baseline; (c) % protection of acute bronchoconstrictor response (ABR) and (d) % protection of airway hyperresponsiveness (AHR).

$$SR_L \text{ (\% change)} = \frac{\text{post challenge } SR_L - \text{baseline } SR_L}{\text{baseline } SR_L} \times 100 \quad (a)$$

$$PD_4 \text{ (\% baseline)} = \frac{\text{post challenge } PD_4}{\text{baseline } PD_4} \times 100 \quad (b)$$

$$ABR \text{ \% protection} = \frac{\text{control } \Delta SR_L \% - LMWHF \Delta SR_L \%}{\text{control } \Delta SR_L \%} \times 100 \quad (c)$$

$$AHR \text{ \% protection} = \frac{LMWHF\ PD_4 - \text{CONTROL ANTIGEN } PD_4}{\text{baseline } PD_4 - \text{control antigen } PD_4} \times 100 \quad (d)$$

The comparative effects of pretreatment with the test materials on ABR and AHR are set forth in Tables 2–6 and are graphically illustrated in FIGS. 1–8.

Figure 1:
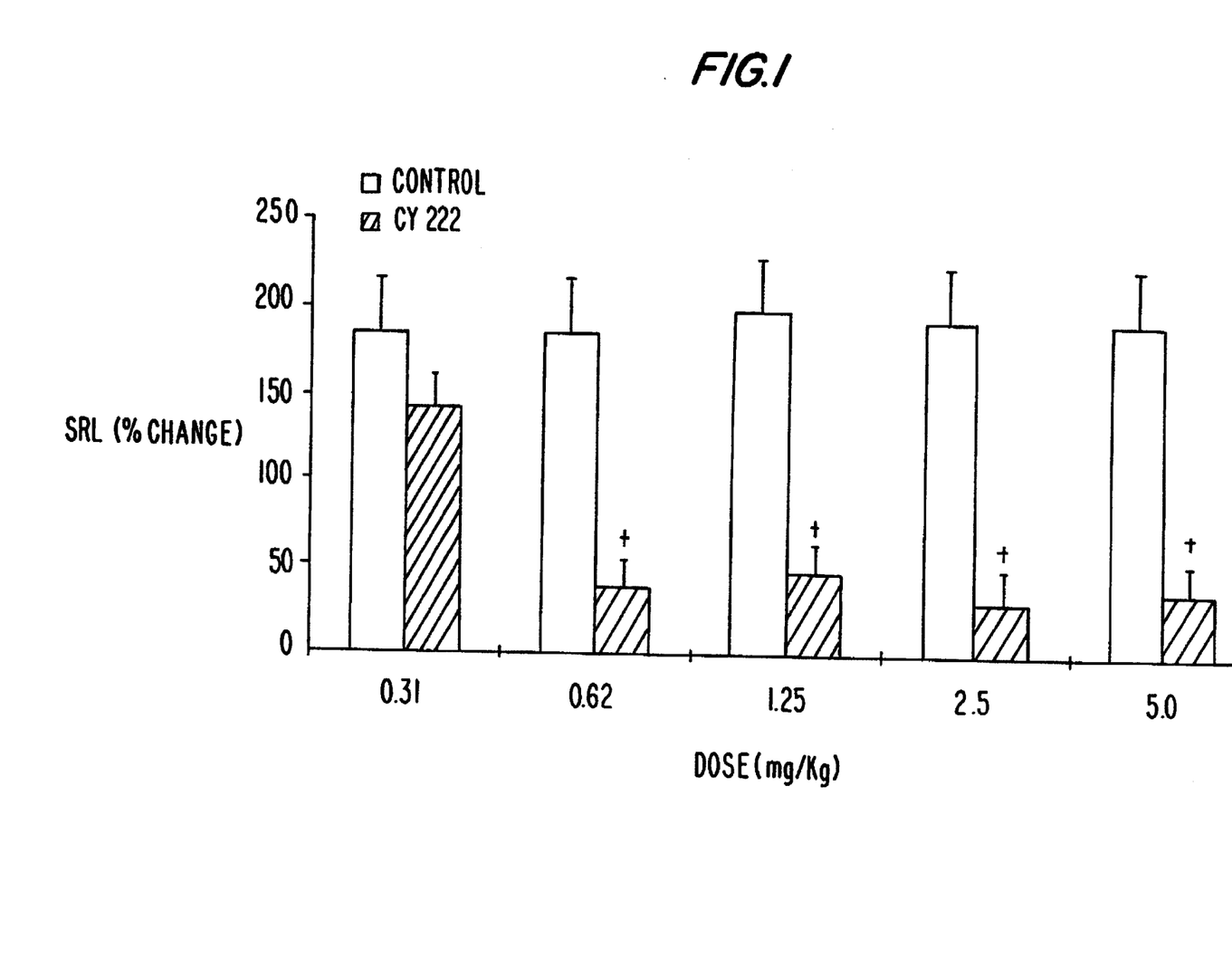
FIG. 1 is a bar graph illustrating the effect of pretreatment with inhaled ultra-low molecular weight heparin (CY222) at varying dose levels on antigen-induced acute bronchoconstriction in allergic sheep. Data are shown as antigen-induced mean±SE % change in $SR_L$, without and after pretreatment with CY222.
Figure 2:
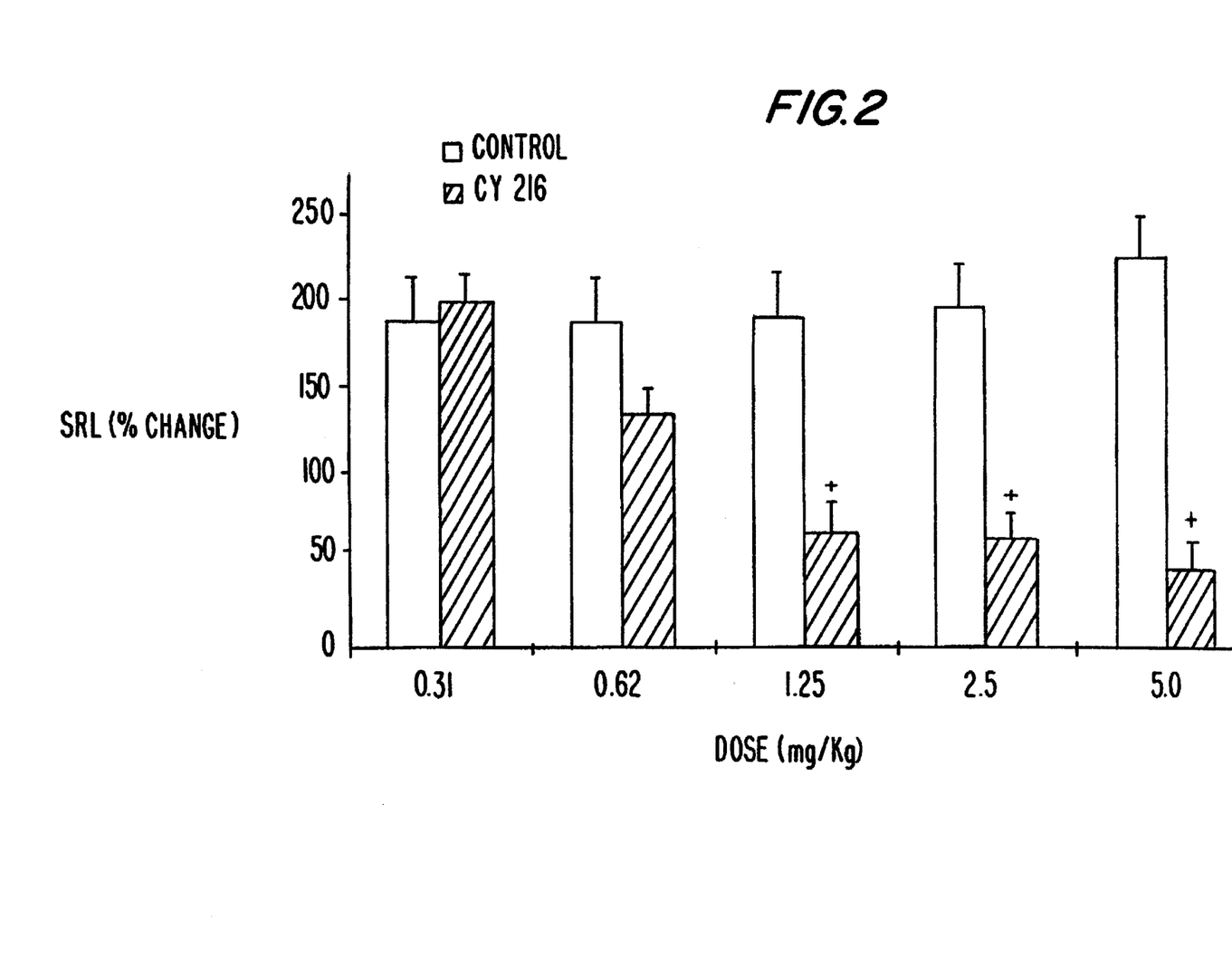
FIG. 2 is a bar graph illustrating the effect of pretreatment with inhaled low molecular weight heparin (CY216) on antigen-induced acute bronchoconstriction in allergic sheep. Data are shown as antigen-induced mean±SE % change in $SR_L$, without and after pretreatment with CY216.
Figure 3:
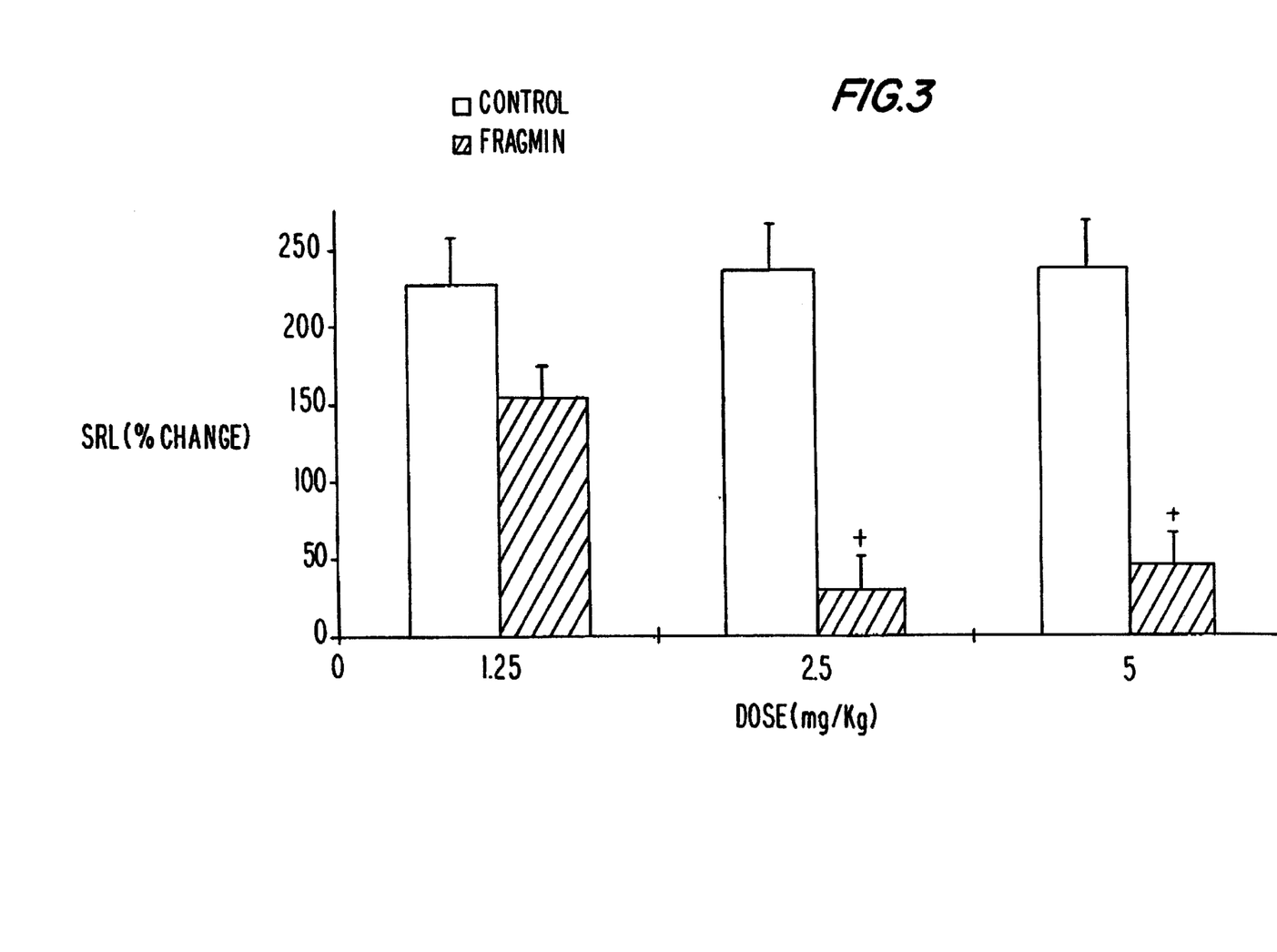
FIG. 3 is a bar graph illustrating the effect of pretreatment with inhaled medium molecular weight heparin (Fragmin) on antigen-induced bronchoconstriction in allergic sheep. Data are shown as antigen-induced mean±SE % change in $SR_L$, without and after treatment with Fragmin.

The data show that pretreatment with aerosolized CY222, CY216 and Fragmin attenuated the antigen-induced acute bronchoconstrictor response in a dose dependent fashion; the minimal effective doses were 0.62 mg/kg, 1.25 mg/kg and 2.5 mg/kg, respectively.

Figure 4:
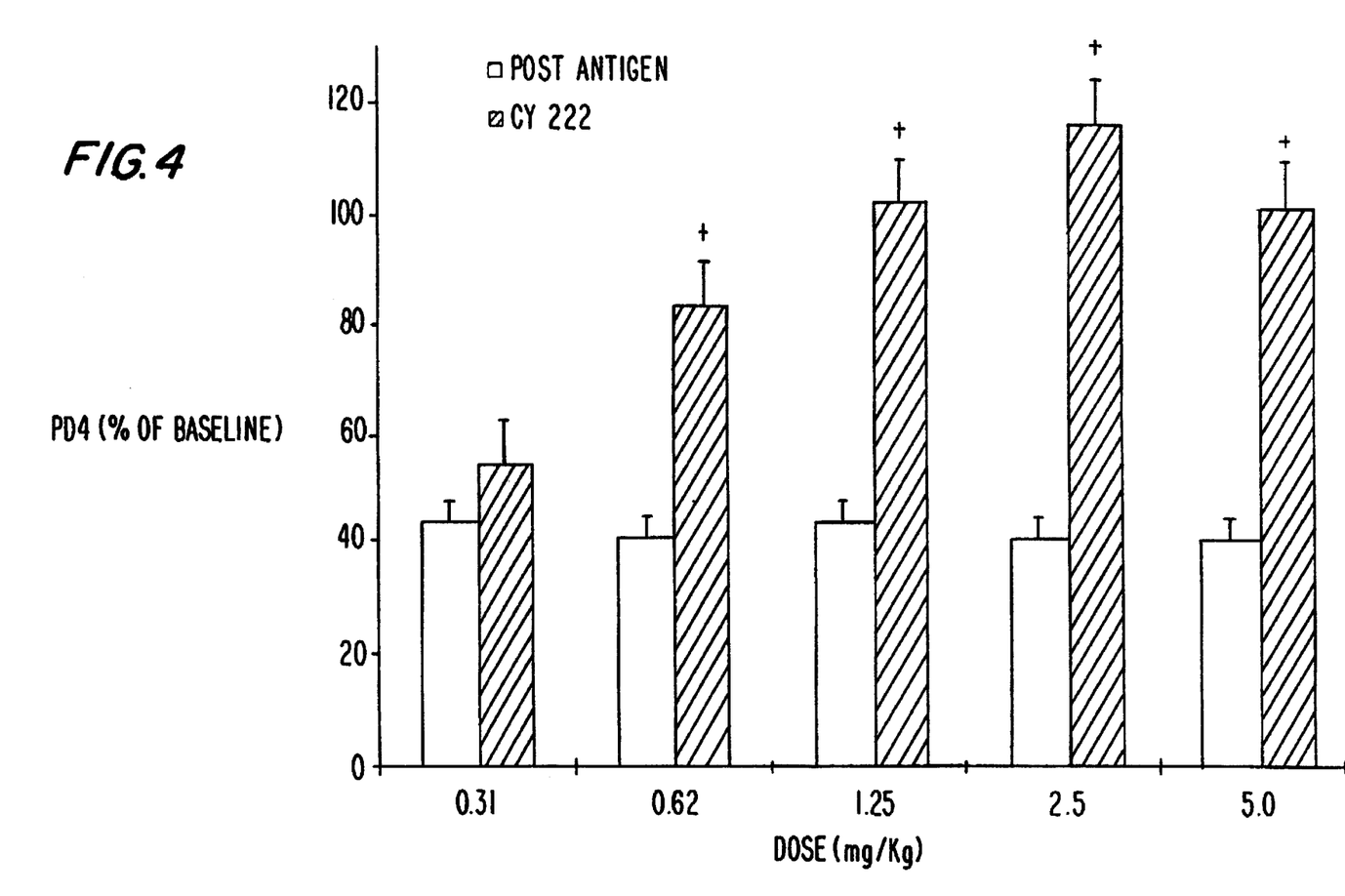
FIG. 4 is a bar graph illustrating the effect of pretreatment with inhaled ultra-low molecular weight heparin (CY222) on antigen-induced airway hyperresponsiveness in allergic sheep. Data are shown as post-antigen mean±SE $PD_4$, as percentage of baseline, without and after pretreatment with CY222.
Figure 5:
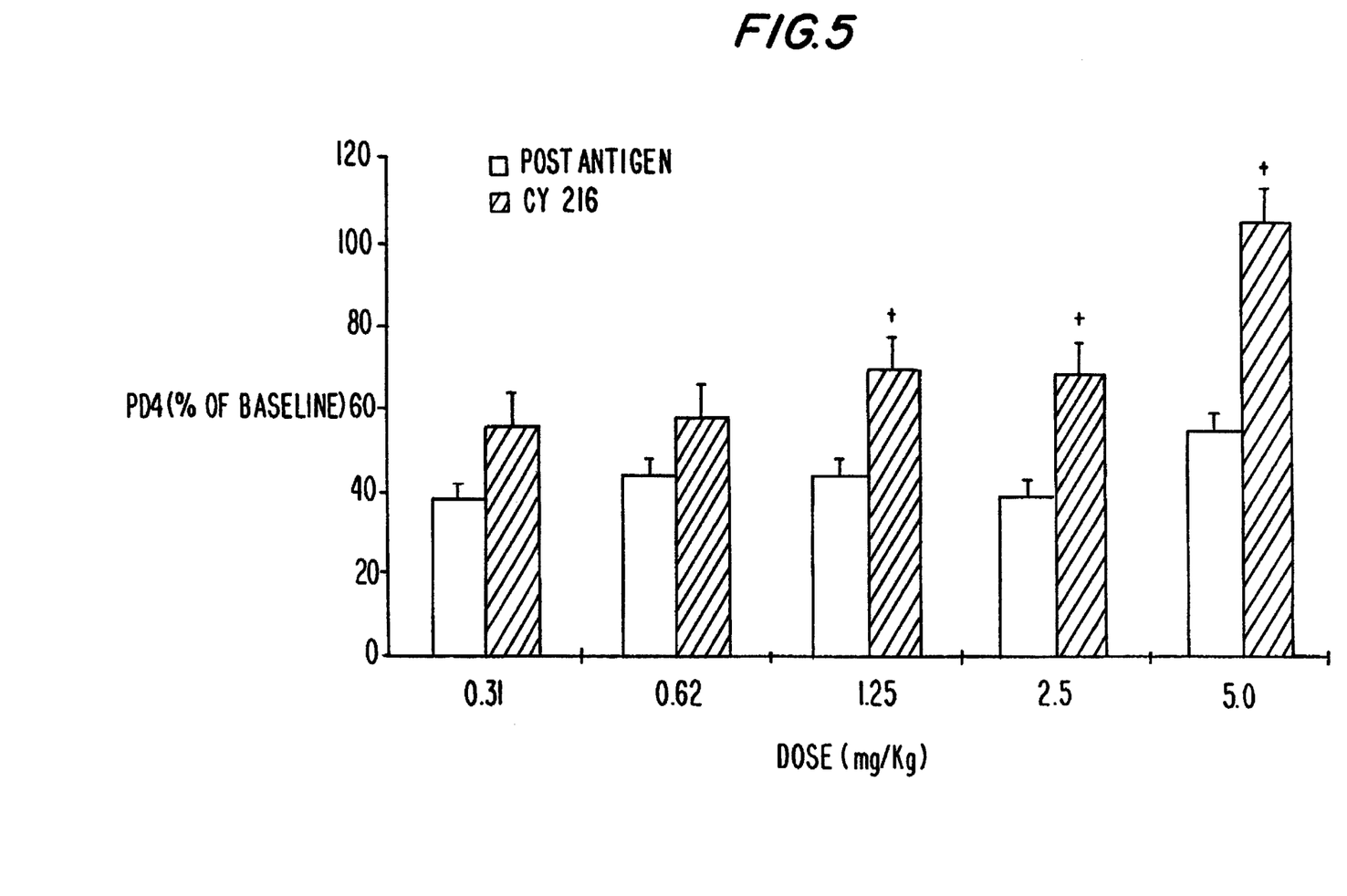
FIG. 5 is a bar graph illustrating the effect of pretreatment with inhaled low molecular weight heparin (CY216) on antigen-induced airway hyperresponsiveness in allergic sheep. Data are shown as post-antigen mean±SE $PD_4$, as percentage of baseline, without and after pretreatment with CY216.
Figure 6:
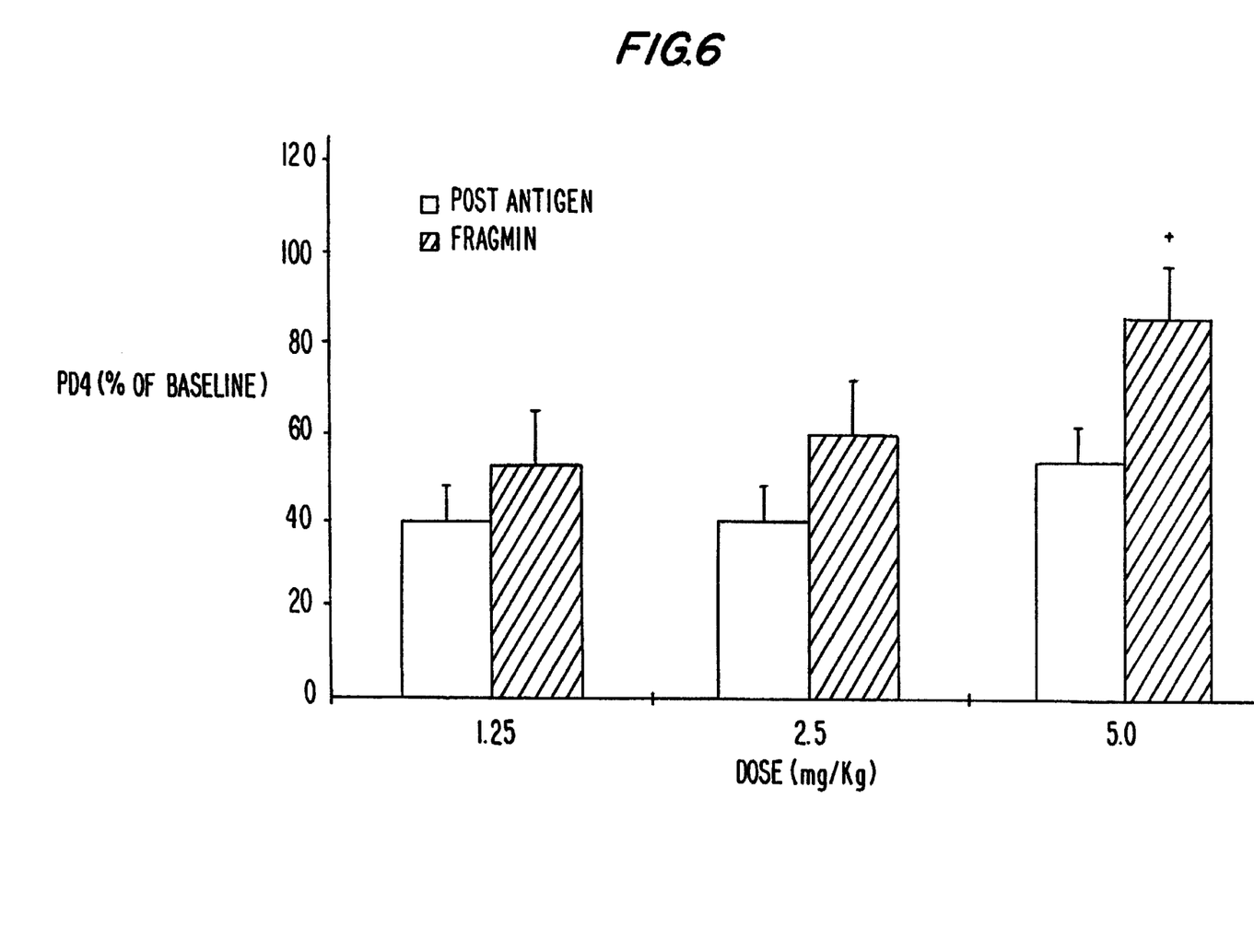
FIG. 6 is a bar graph illustrating the effect of pretreatment with inhaled medium molecular weight heparin (Fragmin) on antigen-induced airway hyperresponsiveness in allergic sheep. Data are shown as post-antigen mean±SE $PD_4$, as percentage of baseline, without and after pretreatment with Fragmin.

Pretreatment with aerosolized CY222, CY216, and Fragmin attenuated the antigen-induced AHR in a dose dependent fashion; the minimal effective doses were 0.62 mg/kg, 1.25 mg/kg, and 5.0 mg/kg; respectively.

Figure 7:
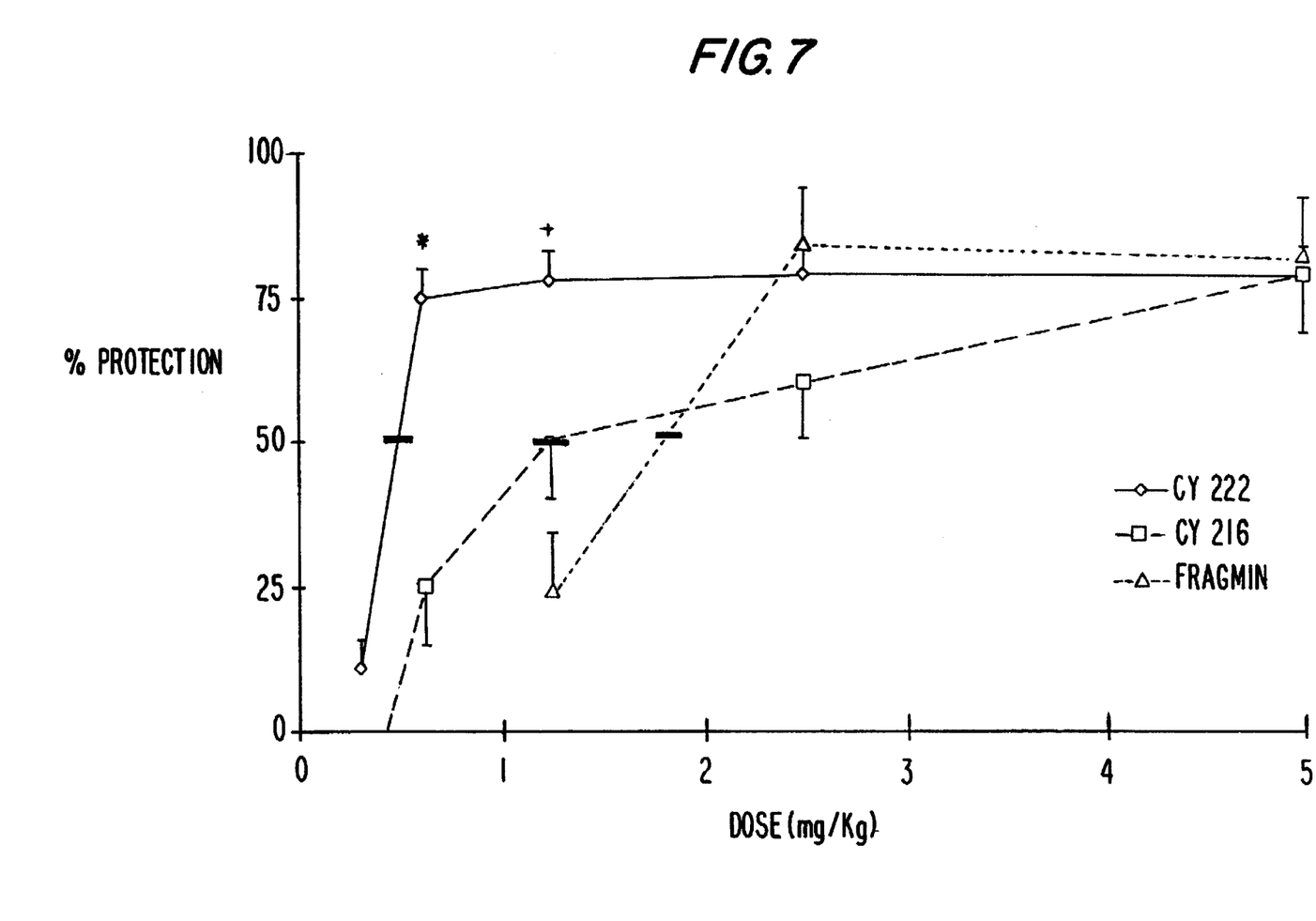
FIG. 7 is a graph illustrating the comparative protective effects of inhaled CY222, CY216 and Fragmin on antigen-induced acute bronchoconstrictor response (ABR) in allergic sheep. Data are shown as post-antigen mean±SE % protection of antigen-induced ABR. Thick horizontal bars represent $ID_{50}$.
Figure 8:
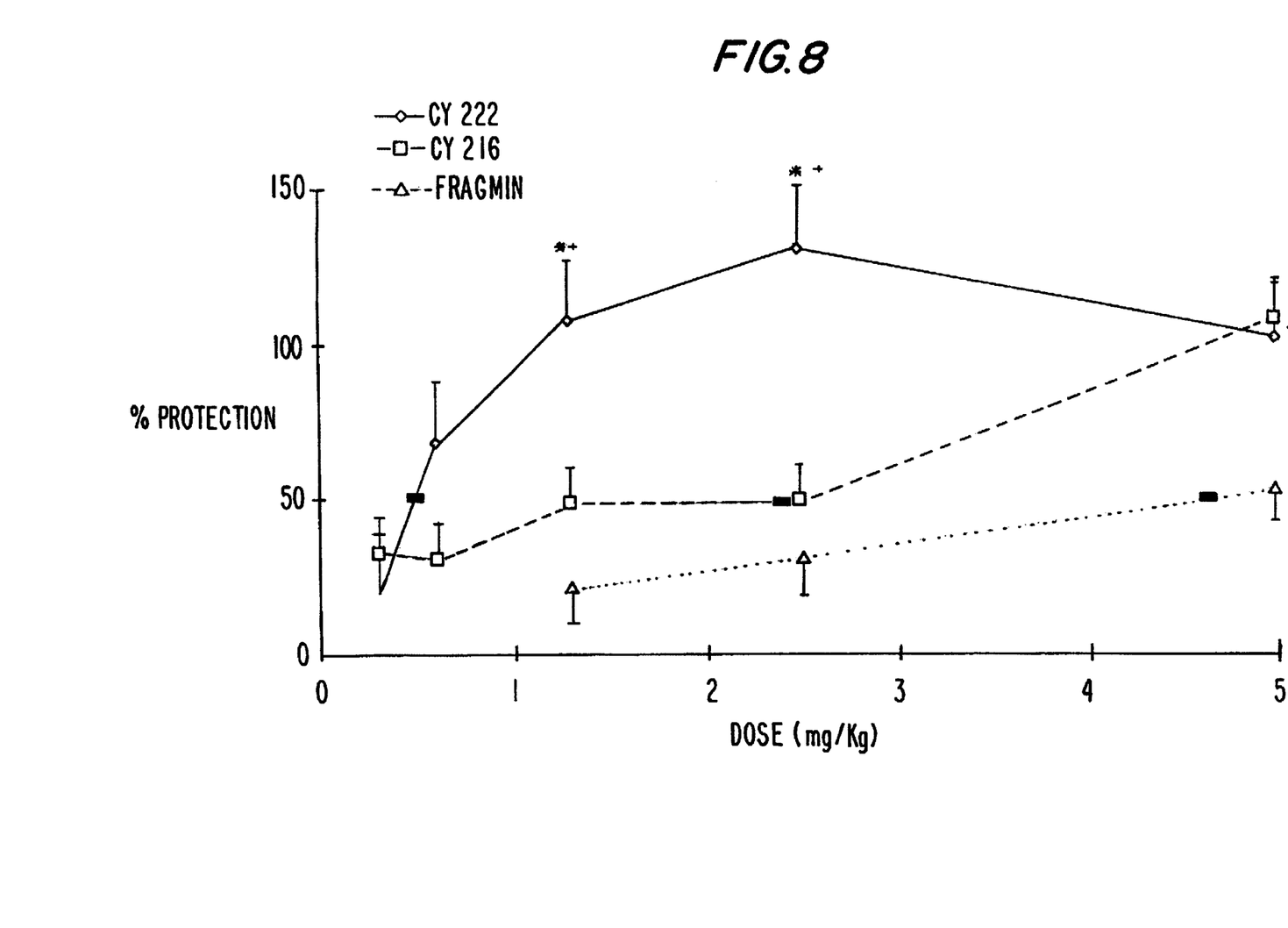
FIG. 8 is a graph illustrating the comparative protective effects of inhaled CY222, CY216 and Fragmin on antigen-induced airway hyperresponsiveness (AHR) in allergic sheep. Data are shown as post-antigen mean±SE % protection of antigen-induced changes in $PD_4$.

Analysis of interdrug comparison revealed that the protective effects were inversely related to the molecular weight of the heparin fractions. The ULMWH fraction, CY222, was the most potent agent, as shown by significant inhibition of antigen-induced bronchoconstriction and AHR at 0.6 mg/kg dose, while CY216 and Fragmin were ineffective at this dose. The group average values of I.D.$_{50}$ of CY222, CY216 and Fragmin against allergic bronchoconsriction were 0.5, 1.3 and 1.8 mg/kg, respectively. The respective group average values of I.D.$_{50}$ of CY222, CY216 and Fragmin against AHR were 0.51, 2.5 and 4.7 mg/kg.

TABLE 2

EFFECT OF PRETREATMENT WITH CY222 ON ANTIGEN-INDUCED BRONCHOCONSTRICTION

| | ANTIGEN-CONTROL | | CY222 | |
|---|---|---|---|---|
| Dose (mg/kg) | Baseline | Post-Challenge | Baseline | Post-CY222 | Post-Challenge |
| 0.31 | 1.15 | 3.27* | 1.17 | 1.08 | 2.66* |
| (n = 7) | (.04) | (.33) | (.05) | (.06) | (.35) |
| 0.62 | 1.15 | 3.27* | 1.15 | 1.21 | 1.65+ |
| (n = 7) | (.04) | (.33) | (.05) | (.06) | (.06) |
| 1.25 | 1.16 | 3.43* | 1.08 | 1.17 | 1.71+ |
| (n = 6) | (.04) | (.323) | (.06) | (.05) | (.19) |
| 2.5 | 1.13 | 3.31* | 1.04 | 1.06 | 1.33+ |
| (n = 6) | (.04) | (.39) | (.05) | (.10) | (.09) |
| 5.0 | 1.13 | 3.31* | 1.16 | 1.12 | 1.56+ |
| (n = 6) | (.04) | (.39) | (.05) | (.02) | (.12) |

Data are shown as mean ± SE $SR_L$ (specific lung resistance), without and after pretreatment with increasing doses led CY222.
* Significantly different from baseline (P < .05)
+ Significantly different from antigen-control (P <.05)

TABLE 3

EFFECT OF PRETREATMENT WITH CY216 ON ANTIGEN-INDUCED BRONCHOCONSTRICTION

| | ANTIGEN-CONTROL | | CY216 | |
|---|---|---|---|---|
| Dose (mg/kg) | Baseline | Post-Challenge | Baseline | Post-CY216 | Post-Challenge |
| 0.31 | 0.92 | 2.64* | 1.12 | 1.08 | 3.21* |
| (n = 7) | (.04) | (.23) | (.07) | (.04) | (.09) |
| 0.62 | 0.92 | 2.64* | 1.04 | 1.07 | 2.54* |
| (n = 7) | (.04) | (.23) | (.06) | (.03) | (.31) |
| 1.25 | 1.12 | 3.24* | 1.04 | 1.20 | 2.03+ |
| (n = 8) | (.04) | (.29) | (.07) | (.13) | (.36) |

TABLE 3-continued

EFFECT OF PRETREATMENT WITH CY216 ON ANTIGEN-INDUCED BRONCHOCONSTRICTION

| Dose (mg/kg) | ANTIGEN-CONTROL | | CY216 | | |
|---|---|---|---|---|---|
| | Baseline | Post-Challenge | Baseline | Post-CY216 | Post-Challenge |
| 2.5 | 1.14 | 3.36* | 1.05 | 1.04 | 1.76+ |
| (n = 5) | (.05) | (.48) | (.07) | (.11) | (.32) |
| 5.0 | 1.09 | 3.35* | 1.09 | 1.18 | 1.75+ |
| (n = 6) | (.04) | (.14) | (.03) | (.08) | (.20) |

Data are shown as mean ± SE $SR_L$ (specific lung resistance) without and after pretreatment with inhaled CY216.
* Significantly different from baseline (P <.05)
+ Significantly different from antigen-control (P <.05)

TABLE 4

EFFECT OF TREATMENT WITH FRAGMIN ON ANTIGEN BRONCHOCONSTRICTION

| Dose (mg/kg) | ANTIGEN-CONTROL | | FRAGMIN | | |
|---|---|---|---|---|---|
| | Baseline | Post-Challenge | Baseline | Post-Fragmin | Post-Challenge |
| 1.25 | 1.04 | 3.37* | 1.11 | 1.07 | 2.71* |
| (n = 7) | (.06) | (.32) | (.05) | (.08) | (.42) |
| 2.5 | 0.96 | 3.19* | 1.07 | 1.16 | 1.56+ |
| (n = 6) | (.04) | (.30) | (.08) | (.12) | (.25) |
| 5.0 | 1.00 | 3.39* | 0.98 | 0.98 | 1.47+ |
| (n = 7) | (.01) | (.39) | (.03) | (.03) | (.21) |

Data are shown as mean ± SE $SR_L$ (specific lung resistance), without and after pretreatment with inhaled Fragmin.
* Significantly different from baseline (P <.05)
+ Significantly different brom antigen-control (P <.05)

TABLE 5

EFFECT OF PRETREATMENT WITH INHALED CY222, CY216 AND FRAGMIN ON ANTIGEN-INDUCED AIRWAY HYPERRESPONSIVENESS

| Dose (mg/kg) | CY22 | | | CY216 | | | FRAGMIN | | |
|---|---|---|---|---|---|---|---|---|---|
| | BASELINE | CONTROL | DRUG | BASELINE | CONTROL | DRUG | BASELINE | CONTROL | DRUG |
| 0.31 | 15.3 | *6.7 | *8.4 | 19.4 | *7.3 | *10.3 | — | — | — |
| (n = 7) | (0.7) | (0.6) | (1.9) | (2.6) | (1.4) | (2.8) | | | |
| 0.62 | 15.7 | *6.5 | 13.0+ | 19.2 | *8.3 | *11.3 | — | — | — |
| (n = 6) | (0.7) | (0.7) | (1.5) | (2.2) | (1.5) | (2.1) | | | |
| 1.25 | 15.4 | *6.7 | 15.6+ | 15.3 | *6.7 | *10.6+ | 16.7 | *6.4 | *8.7 |
| (n = 7) | (0.6) | (0.6) | (1.6) | (0.7) | (0.6) | (1.3) | (1.8) | (0.7) | (1.8) |
| 2.5 | 15.7 | *6.5 | 18.1+ | 15.4 | *6.1 | *10.7+ | 19.3 | *7.8 | *11.0 |
| (n = 6) | (0.7) | (0.7) | (2.5) | (0.7) | (0.7) | (1.7) | (3.0) | (1.6) | (1.2) |
| 5.0 | 15.7 | *6.5 | 15.9+ | 15.7 | *8.5 | 16.4+ | 19.4 | *10.5 | 16.6+ |
| (n = 6) | (0.7) | (0.7) | (0.5) | (1.0) | (0.7) | (1.4) | (2.7) | (2.1) | (2.9) |

Data are shown as mean ± SE $PD_4$ of carbachol in breath units, for the baseline and post-antigen, without (control) and after pretreatment (drug) with various heparin fractions.
$PD_4$ = Cummulative provocating dose of carbachol which increased $SR_L$ to 400% above baseline.
*Significantly different from baseline (P < .05)
+ Significantly different from antigen control (P < 0.5)

TABLE 6

COMPARISON OF PROTECTIVE EFFECT OF INHALED CY222 (ULTRALOW MOLECULAR WEIGHT); CY216 (LOW MOLECULAR WEIGHT) AND FRAGMIN (MEDIUM MOLECULAR WEIGHT) ON ANTIGEN-INDUCED BRONCHOCONSTRICTION AND AIRWAY HYPERRESPONSIVENESS

| Dose (mg/kg) | ALLERGIC BRONCHOCONSTRICTION | | | Dose (mg/kg) | AIRWAY HYPERRESPONSIVENESS | | |
|---|---|---|---|---|---|---|---|
| | CY222 | CY216 | FRAGMIN | | CY222 | CY216 | FRAGMIN |
| 0.31 | 11% | −16% | 24% | 0.31 | 18% | 32% | — |
| | (21%) | (14%) | | | (21%) | (17%) | |
| 0.62 | 75%†* | 25% | — | 0.62 | 68%† | 30% | — |
| | (8%) | (15) | | | (18%) | (11%) | |
| 1.25 | 78%†+ | 50%† | 24% | 1.25 | *107%*†+ | 48%† | 21% |
| | (8%) | (20%) | (20%) | | (26%) | (12%) | (12%) |
| 2.5 | 79%† | 60%† | 84%† | 2.5 | *131%†+ | 49%† | 30% |
| | (9%) | (11%) | (9%) | | (35%) | (12%) | (11%) |

TABLE 6-continued

COMPARISON OF PROTECTIVE EFFECT OF INHALED CY222 (ULTRALOW MOLECULAR WEIGHT); CY216 (LOW MOLECULAR WEIGHT) AND FRAGMIN (MEDIUM MOLECULAR WEIGHT) ON ANTIGEN-INDUCED BRONCHOCONSTRICTION AND AIRWAY HYPERRESPONSIVENESS

| Dose (mg/kg) | ALLERGIC BRONCHOCONSTRICTION | | | Dose (mg/kg) | AIRWAY HYPERRESPONSIVENESS | | |
|---|---|---|---|---|---|---|---|
| | CY222 | CY216 | FRAGMIN | | CY222 | CY216 | FRAGMIN |
| 5.0 | 79%† (3%) | 79%† (6%) | 82%† (7%) | 5.0 | 102%†+ (8%) | 108%†+ (15%) | 53%† (16%) |
| I.D.$_{50}$ | 0.5 mg/kg | 1.1 mg/kg | 1.8 mg/kg | I.D.$_{50}$ | 0.5 mg/kg | 2.5 mg/kg | 4.7 mg/kg |

Data are shown as mean ± SE % protection at each dose. Calculated group average I.D.$_{50}$ (inhibiting dose causing 50% protection) is also shown for each group.
† Significant protection ($P < .05$)
+ Significantly different from Fragmin ($P < .05$)
*Significantly different from CY216 ($P < .05$)

EXAMPLE II

Administration of Heparins Following Antigen Challenge

Figure 9:
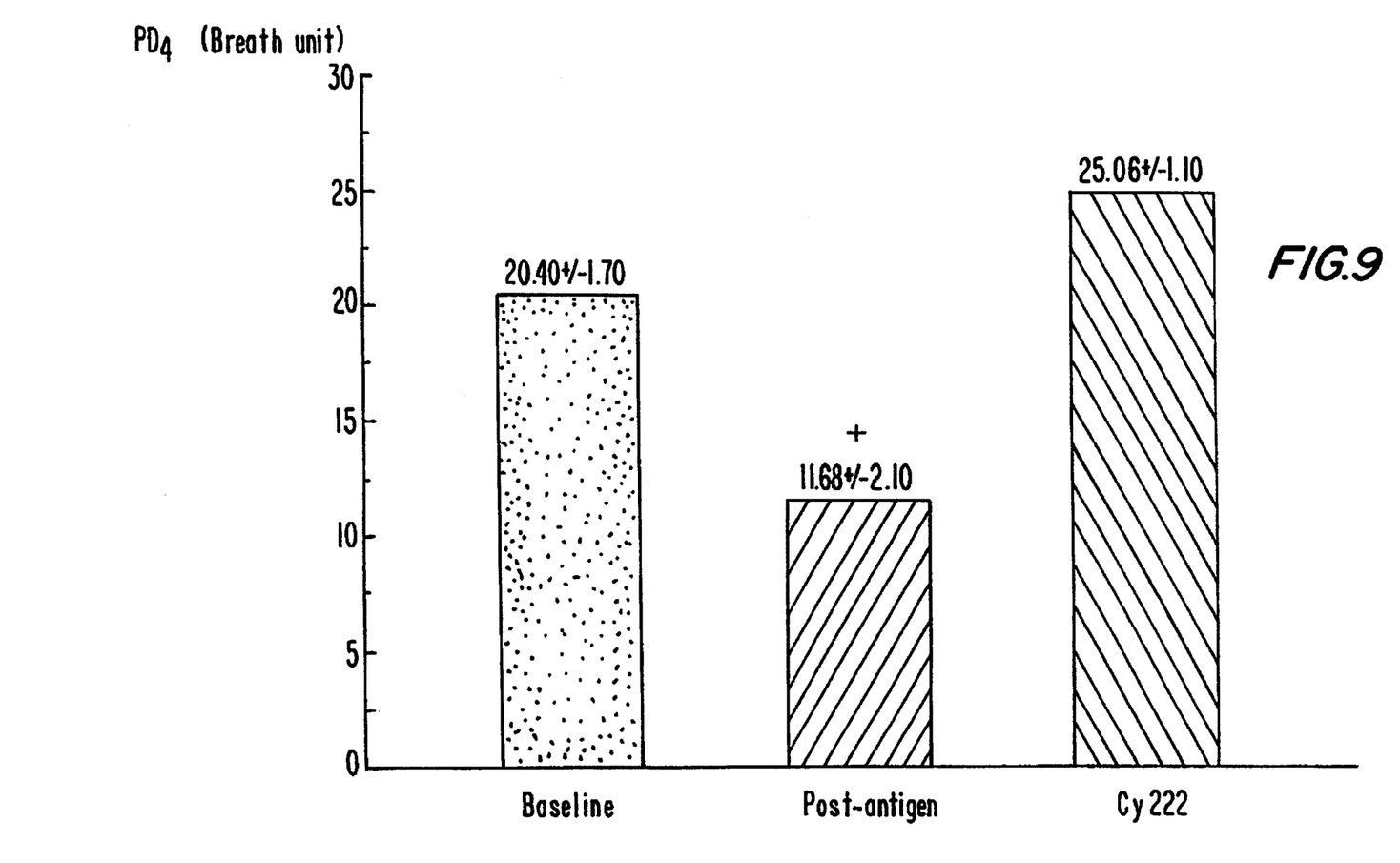
FIG. 9 is a bar graph illustrating the effect of CY222 on antigen-induced airway hyperresponsiveness with CY222 being administered as an aerosol immediately after antigen challenge.
Figure 10:
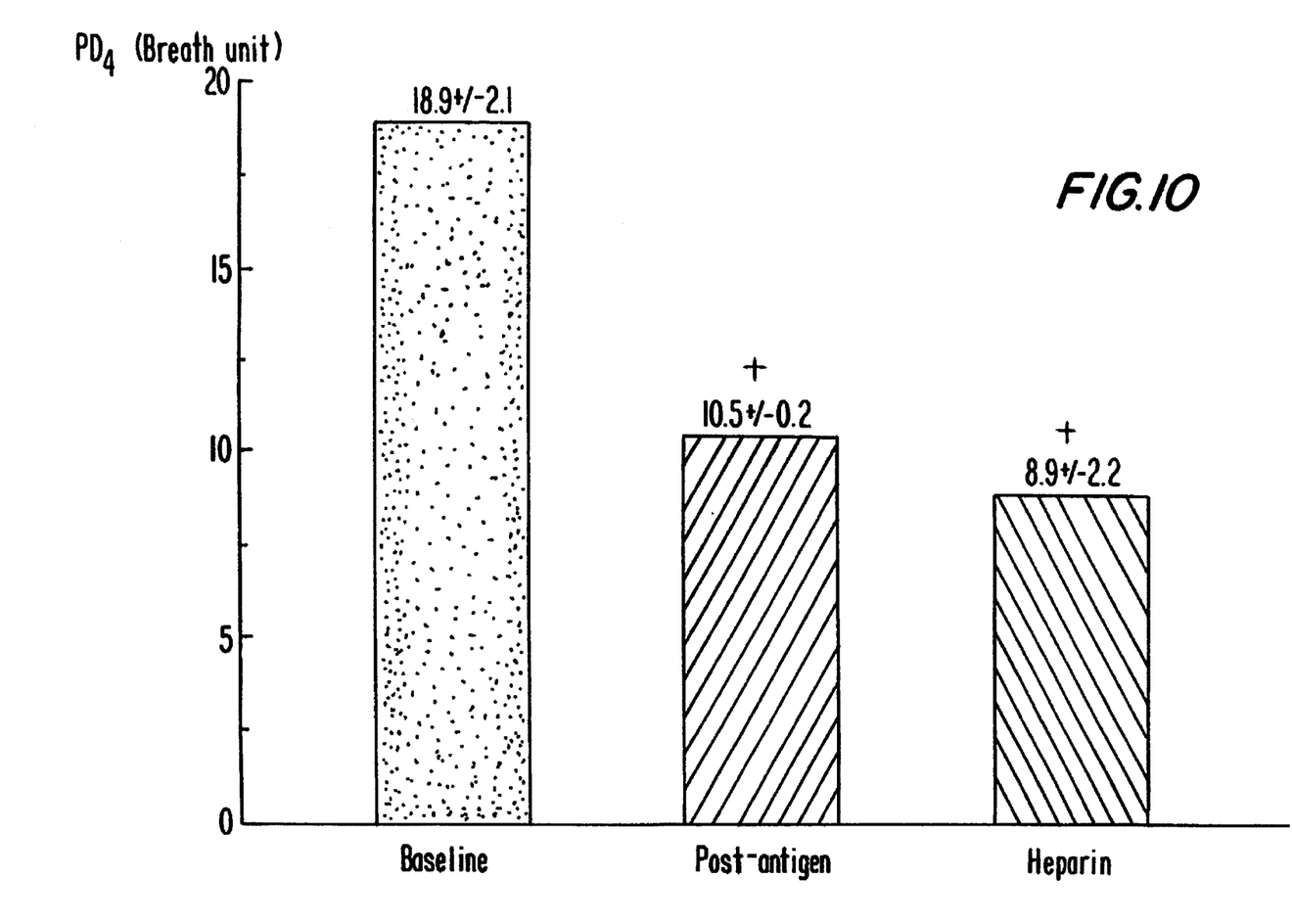
FIG. 10 is a bar graph illustrating the effect of commercial heparin on antigen-induced airway hyperresponsiveness with commercial heparin being administered as an aerosol immediately after antigen challenge.
Figure 11:
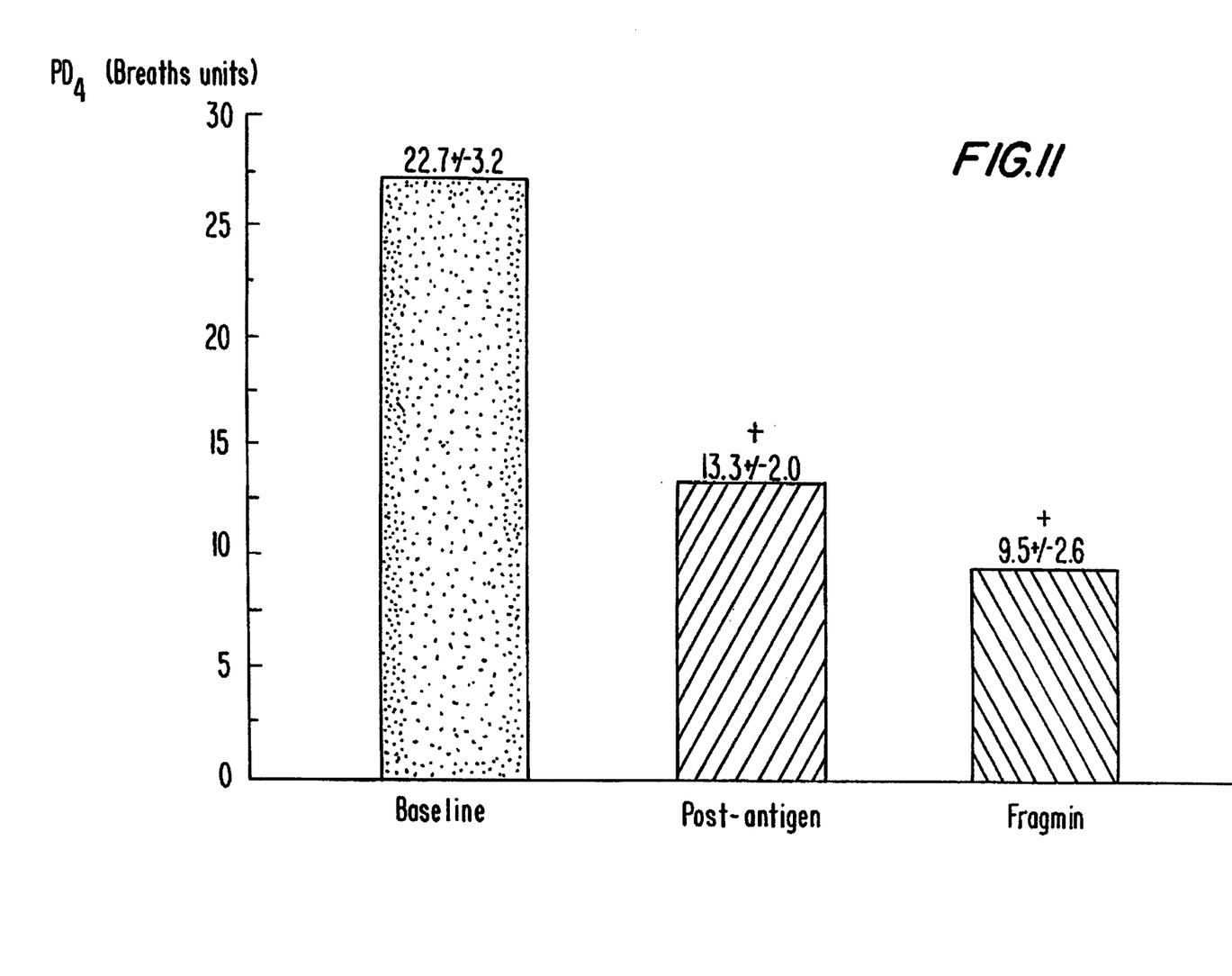
FIG. 11 is a bar graph illustrating the effect of Fragmin on antigen-induced airway hyperresponsiveness with Fragmin being administered as an aerosol immediately after antigen challenge.

The same experimental protocol was followed as in Example I, except that (a) the three heparin materials administered to the test animals were CY222, commercial heparin (molecular weight approximately 15,000 daltons) and Fragmin, and (b) the heparins were administered to the animals as an aerosol immediately after antigen challenge. The test data are set forth in Table 7 and graphically illustrated in FIGS. 9–11.

TABLE 7

COMPARATIVE EFFECTS OF INHALED COMMERCIAL HEPARIN (8 MG/KG), MEDIUM MOLECULAR WEIGHT HEPARIN FRACTION (FRAGMIN, 5 MG/KG) AND ULTRA LOW-MOLECULAR WEIGHT HEPARIN FRACTION (CY222, 0.6 MG/KG) ON ANTIGEN-INDUCED AIRWAY HYPERRESPONSIVENESS.

| | Baseline | Post Antigen (control) | Post-Antigen (heparin) |
|---|---|---|---|
| Heparin | 18.9 ± 2.1 | 10.5 ± 0.2* | 8.9 ± 2.2* |
| Fragmin | 22.7 ± 3.2 | 13.3 ± 2.0* | 9.5 ± 2.6* |
| CY222 | 20.4 ± 1.7 | 11.7 ± 2.1* | 25.1 ± 1.1+ |

Data are shown as mean ± SE PD$_{400}$ of carbachol in breath units (one breath unit is equivalent of one breath of 1 mg/ml carbachol). All agents were nebulized immediately "after" the antigen challenge.
*Significantly different from baseline ($p < .05$)
+Significantly different from antigen-control ($p < .05$)
Only CY22 offered significant protection As indicated by Table 7 and FIGS. 9–11, inhaled CY222 administered after antigen challenge substantially modified post-antigen AHR, restoring AHR levels in the test subjects to baseline levels or above. This effect was not observed with commercial heparin or Fragmin, wherein no improvement in AHR resulted from post-challenge administration of these heparins.

It has thus been shown that there have been provided methods and compositions which achieve the various objects of the invention and which are well adapted to meet the conditions of practical use.

As various possible embodiments might be made of the above invention, and as various changes might be made in the embodiments set forth above, it is to be understood that all matters herein described are to be interpreted as illustrative and not in a limiting sense.

What is claimed as new and desired to be protected by Letters Patent is set forth in the following claims:

1. A method of treating a patient suffering from antigen-induced asthma who has been challenged with an asthma-inducing antigen consisting essentially of the intrabronchial administration to the patient after the antigen challenge of a pharmaceutical composition containing about 0.05 to about 1.0 mg of ultra-low molecular weight heparins (ULMWH) per kilogram of patient body weight in each dose, said ULMWH having an average molecular weight of 3,000 daltons or less.

2. A method according to claim 1 wherein said ULMWH have an average molecular weight of 2,500 daltons or less.

3. A method according to claim 1 wherein said composition contains about 0.075 to about 0.75 mg of ULMWH per kilogram per dose.

4. A method according to claim 1 wherein said composition contains about 1.0 to about 20.0 mg of ULMWH per ml of composition.

5. A method according to claim 1 wherein said ULMWH have no anticoagulant activity.

6. A method according to claim 1 wherein each of said ULMWH comprises disaccharides, trisaccharides, tetrasaccharides or pentasaccharides.

7. A method according to claim 1 wherein said composition comprises a solution of ULMWH in an aqueous, pharmaceutically acceptable inhalant vehicle.

8. A method according to claim 7 wherein said vehicle is isotonic saline or bacteriostatic water.

9. A method according to claim 7 wherein said composition is administered by means of a pump or squeeze-actuated nebulizer.

10. A method according to claim 7 wherein said composition further includes an aerosol propellant and is administered via a metered aerosol dose inhaler.

11. A method according to claim 1 wherein said composition comprises a powdered preparation of ULMWH intermixed with an inert powder acceptable for intrabronchial administration.

12. A method according to claim 11 wherein said inert powder is lactose.

13. A method according to claim 11 wherein said composition is administered via an aerosol dispenser.

14. A method according to claim 11 wherein said composition is administered from a breakable capsule.

15. A method of treating a patient suffering from asthma consisting essentially of the intrabronchial administration on a chronic basis to the patient of a pharmaceutical composition containing about 0.05 to about 1.0 mg of ultra-low molecular weight heparins (ULMWH) per kilogram of patient body weight in each dose, said ULMWH having an average molecular weight of 3,000 daltons or less.

16. A method according to claim 15 wherein said ULMWH have an average molecular weight of 2,500 daltons or less.

17. A method according to claim 15 wherein said composition contains about 0.075 to about 0.75 mg of ULMWH per kilogram per dose.

18. A method according to claim 15 wherein said composition contains about 1.0 to about 20.0 mg of ULMWH per ml of composition.

19. A method according to claim 15 wherein said ULMWH have no anticoagulant activity.

20. A method according to claim 15 wherein each of said ULMWH comprises disaccharides, trisaccharides, tetrasaccharides or pentasaccharides.

* * * * *